United States Patent
Zenker

(10) Patent No.: US 10,124,122 B2
(45) Date of Patent: Nov. 13, 2018

(54) ATTACHMENT FOR A SYRINGE, CARPULE OR THE LIKE

(71) Applicant: VETTER PHARMA-FERTIGUNG GmbH & Co. KG, Ravensburg (DE)

(72) Inventor: Jochen Zenker, Ravensburg (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 497 days.

(21) Appl. No.: 14/774,201

(22) PCT Filed: Mar. 4, 2014

(86) PCT No.: PCT/EP2014/054142
§ 371 (c)(1),
(2) Date: Sep. 10, 2015

(87) PCT Pub. No.: WO2014/139832
PCT Pub. Date: Sep. 18, 2014

(65) Prior Publication Data
US 2016/0022925 A1    Jan. 28, 2016

(30) Foreign Application Priority Data
Mar. 11, 2013 (DE) .......... 10 2013 204 134

(51) Int. Cl.
*A61M 5/34* (2006.01)
*A61M 39/10* (2006.01)
*A61M 5/31* (2006.01)

(52) U.S. Cl.
CPC .............. *A61M 5/34* (2013.01); *A61M 5/343* (2013.01); *A61M 5/344* (2013.01); *A61M 5/345* (2013.01);
(Continued)

(58) Field of Classification Search
CPC ...... A61M 5/349; A61M 5/348; A61M 5/347; A61M 5/345; A61M 5/344; A61M 5/343;
(Continued)

(56) References Cited

U.S. PATENT DOCUMENTS

2011/0282295 A1    11/2011  Pupke et al.
2012/0157928 A1*   6/2012   Mermet ............... A61M 5/344
                                                              604/187

FOREIGN PATENT DOCUMENTS

DE    102004040969 A1   3/2006
DE    202009016091 U1   3/2010
(Continued)

OTHER PUBLICATIONS

International Search Report for PCT/EP2014/054142, dated Jun. 10, 2014 with English translation.
(Continued)

*Primary Examiner* — Bhisma Mehta
*Assistant Examiner* — Anh Bui
(74) *Attorney, Agent, or Firm* — Stephen T. Olson; Harness, Dickey & Pierce, P.L.C.

(57) ABSTRACT

An attachment for a syringe or carpule includes a main body that encloses an interior space, into which a protrusion of the syringe or carpule can be inserted. The main body has a jacket surrounding the interior space, and includes an inner body connected to the jacket and arranged coaxially thereto. The inner body has an inner wall that, in the attached state of the attachment, contacts an outer surface of the protrusion or of the syringe or carpule by means of an interior surface facing the interior space. The inner wall of the inner body is connected to the jacket of the attachment by a number of webs. At least one web encloses an angle together with an imaginary radially extending line, the angle being greater than 0° and acute.

19 Claims, 4 Drawing Sheets

(52) U.S. Cl.
CPC ............ *A61M 5/348* (2013.01); *A61M 5/349* (2013.01); *A61M 39/1011* (2013.01); *A61M 5/347* (2013.01); *A61M 2005/312* (2013.01); *A61M 2005/3103* (2013.01); *A61M 2005/3104* (2013.01)

(58) Field of Classification Search
CPC ................ A61M 5/34; A61M 39/1011; A61M 2005/312; A61M 2005/3104; A61M 2005/3103
See application file for complete search history.

(56) References Cited

FOREIGN PATENT DOCUMENTS

| | | |
|---|---|---|
| DE | 102009007250 A1 | 7/2010 |
| EP | 2016962 A1 | 1/2009 |
| WO | WO-2009/092430 A1 | 7/2009 |

OTHER PUBLICATIONS

Written Opinion of the ISA for PCT/EP2014/054142, dated Jun. 10, 2014.

English Translation of the International Preliminary Report on Patentability (Ch. I) for PCT/EP2014/054142, IB, Geneva, dated Sep. 15, 2015, incorporating the English translation of the Written Opinion of the ISA, ISA/EP, Rijswijk, NL, dated Jun. 10, 2014.

\* cited by examiner

ATTACHMENT FOR A SYRINGE, CARPULE OR THE LIKE

CROSS-REFERENCE TO RELATED APPLICATIONS

This application is a 371 U.S. National Stage of International Application No. PCT/EP2014/054142, filed Mar. 4, 2014. This application claims the benefit of and priority to German Patent Application No. 10 2013 204 134.9, filed Mar. 11, 2013. The disclosures of the above applications are incorporated herein by reference.

FIELD

The invention relates to an attachment for a syringe or carpule.

BACKGROUND

Attachments for syringes, carpules and the like are known. They are also used as adapters, and serve to provide a fastening means for a cannula or other device, such as an injection device or the like. They are attached and fixed on a protrusion of the syringe, carpule or the like. They generally comprise an inner thread, into which a projection of a cannula or the like can be screwed. Attachments of the type discussed here are frequently designed as safety or guarantee seals and have a fixing part which is firmly attached to a terminal protrusion of a syringe, a carpule or the like and lockingly held there. In such seals, a cap is connected via a predetermined rupture line with the fixing part, the cap securely covering the free end of the protrusion, which is directed away from the syringe, carpule or the like, whereby the interior space of the syringe, carpule or the like is also protected. When the cap is removed, the predetermined rupture line rips open, so that it can be irreversibly seen that the cap has been removed. Protection against manipulation of the attachment is thereby ensured. The protrusion comprises a free end, preferably also at least one recess at a distance therefrom which is introduced in the outer surface of the protrusion, the recess being preferably formed as an annular groove. The attachment fixed on the syringe, carpule or the like lockingly engages therein. The invention mentioned here relates both to attachments with a safety cap as well as those without such tamper security. It has been found that attachments of the type mentioned here can often perform a relative rotation with respect to the protrusion of the syringe, carpule or the like under the effect of rotational torque, and may thereby become detached, so that the medium present within the syringe, carpule or the like is contaminated and becomes unusable. This can result in substantial financial losses or cause harm to patients.

SUMMARY

The object of the invention is therefore to design an attachment of the type referred to herein such that it can be mounted securely on a syringe or carpule, wherein a relative rotation between the attachment and the syringe or carpule can be avoided with a high degree of security.

To achieve this object, an attachment of the type discussed here is provided which comprises an interior space-enclosing main body comprising a jacket and a coaxially arranged inner body connected thereto. The attachment is characterized in that the inner wall of the inner body, which in the attached state of the attachment contacts the protrusion of a syringe or carpule, is connected to the jacket of the attachment by a number of webs, which encloses an angle with an imaginary radially extending line which intersects or touches an end of the web. The angle is greater than 0° and acute. If rotational torque is introduced in such an attachment, a web extending at an angle to an imaginary radial line pivots such that the web extends radially and is thus compressed between the jacket and the inner wall of the inner body. This results in that the inner wall is pressed and securely held against the protrusion of the syringe, carpule or the like with increased force, so that a rotation of the attachment with respect to the protrusion is avoided with a high degree of security.

A preferred embodiment of the attachment is characterized by at least one abutment, which originates from the inner side of the jacket and is arranged at a distance from a web. The abutment is arranged here such that when rotational torque acts on the attachment, a web can be pivoted out of its position, in which it is arranged at an acute angle to an imaginary radial line, to a maximum position in which it extends radially and thus exerts maximum contact pressure on the protrusion. If, however, it is pivoted beyond the radial line, this leads to a reduction of the forces which press the inner wall against the protrusion. This is prevented by means of the abutment such that, when rotational torque acts on the attachment, webs can be pivoted up to the position in which a maximum contact force is exerted, and then held in this position by means of the abutment.

A further preferred embodiment is characterized in that the abutment has a lateral projection which extends in the circumferential direction toward the associated web and thus results in a defined contact position of the web on the abutment. The forces acting on the web can thus be predetermined, so that the behavior of an attachment upon the introduction of rotational torque can be precisely predetermined.

In a further preferred embodiment, two abutments are provided, so that more than one web can be prevented from pivoting over the radial position. It is, however, also conceivable to arrange abutments such that they brace the webs of an attachment against undesired rotation in both directions.

Further embodiments of the attachment are apparent from the dependent claims.

BEST DESCRIPTION OF THE DRAWINGS

The invention will be explained in more detail below with reference to drawings.

DETAILED DESCRIPTION

Figure 1:
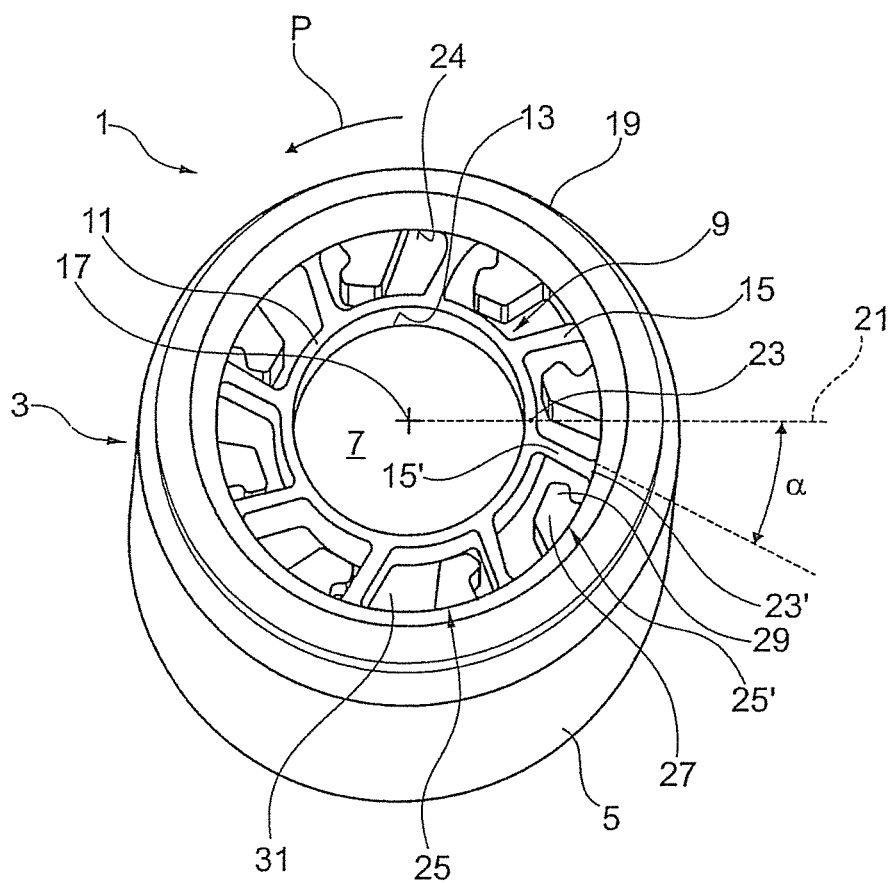
FIG. 1 shows a schematic diagram of a first embodiment of an attachment in a perspective view from below.

The first embodiment of an attachment shown in FIG. 1 is suitable for syringes or carpules and comprises a main body 3, the jacket 5 of which surrounds an interior space 7. An inner body 9 is connected to the jacket 5, the inner body having an inner wall 11 which in the attached state of the attachment 1 contacts with its interior surface 13 the outer surface of a protrusion of a syringe, carpule or the like. The inner wall 11 of the inner body 9 is connected to the jacket 5 by means of a number of webs 15, wherein the webs originate from the inner side of the jacket 5. Its inner body 9 is thus arranged coaxially to the jacket 5.

The main body 3 of the attachment 1 comprises a central axis 17, which is perpendicular to an imaginary plane, in which lies the underside 19 of the attachment 1 facing the viewer in FIG. 1. Through the central axis 17 extends an imaginary radially extending line 21, which also extends through one end of a web 15 or through a transition point 23 between one end of a web 15 and an inner wall 11. At least one web 15 extending between jacket 5 and inner body 9 encloses with this line 21 an angle α, which is greater than 0° and acute. This angle opens outward from the transition point 23 in such a way that a concrete web 15' is arranged below the radially extending line 21 in FIG. 1. In the embodiment shown in FIG. 1, all of the webs of the attachment 1 are arranged relative to an imaginary radially extending line 21 such that they have a corresponding orientation to the web 15'.

The embodiment illustrated in FIG. 1 is characterized in that the inner wall 11 is formed continuously, thus comprising a ring, which is held by the webs 15 at a distance from the jacket 5 of the main body 3 of the attachment 1.

The inner diameter of the inner body 9 defined by the interior surface 13 of the inner wall 11 is somewhat smaller than the outer diameter of the protrusion of a syringe, carpule or the like, on which the attachment 1 is to be attached. Thus, when the attachment 1 is attached to the protrusion, not shown here, the inner body 9 is expanded. If, as is preferably provided, the protrusion comprises a preferably annular recess in the region of its outer surface, the interior surface 13 of the inner wall 11 thus snaps into this annular groove during attachment of the attachment 1 on a protrusion, and holds the attachment 1 securely on the protrusion of the syringe, carpule or the like.

At least one of the webs 11 is allocated to an abutment 25, which originates from the inner side 24 of the jacket 5 and extends in the direction of the interior space 7. The abutment 25 comprises a base body 27, which preferably tapers starting from the inner side 24 in the direction of its opposite free end and which comprises on one side a projection 29 preferably originating on the free end, the projection extending in the direction toward the adjacent web, here in the direction of the web 15'.

In the embodiment of the attachment 1 shown here, each web 15 is allocated to such an abutment 25.

Open spaces 31 are created by two adjacent webs 15 and an associated region of the inner wall 11, the open spaces being enclosed by the inner side 24 of the jacket 5 and the interior surfaces of the webs facing the open spaces 31 as well as the inner wall 11.

In the embodiment shown in FIG. 1, eight webs 15 are provided, which are arranged at an equal spacing from one another, arranged in the same angular position relative to an imaginary radially extending line 21, between which webs—seen in the circumferential direction—a respective open space 31 is formed, which is bounded radially outward by the inner side 24 of the jacket 5 and radially inward by the inner side of the inner wall 11 and finally by the interior surfaces of the adjacent webs 15. In each open space 31 is preferably here provided an abutment 25, which comprises a base body 27 and a projection 29, as is described above.

The embodiment described here may be modified such that only two abutments 25 are provided or that only every second open space 31 is allocated an abutment or the like.

Moreover, it is possible not to form the inner wall 11 as a closed ring, but rather to provide ring segments, which are formed by two directly adjacent webs 15 and a section of the inner wall 11, which connects the two webs. Thus, no inner wall is provided right or left of the webs connected by a section of the inner wall 11. The following right and left webs then form further ring segments with the respectively adjacent webs and a section of the inner wall allocated thereto. In other words: The continuous inner wall 11 of FIG. 1, which spans all open spaces 31, is omitted in a modified embodiment from every second open space, so that in an attachment 1 with eight webs 15, four ring segments are then formed. A ring segment may also enclose two adjacent open spaces 31, wherein each of the open spaces is laterally bounded by two adjacent webs, and wherein the central web faces both open spaces.

In such a configuration, it is possible to provide an abutment 25 between two adjacent ring segments and to form the open spaces 31 without such an abutment 25. Furthermore, it is possible to modify the embodiment shown in FIG. 1 in that four ring segments are formed which enclose the open spaces 31, and that abutments are only provided in these enclosed open spaces 31.

It can be seen in FIG. 1 that the abutments 25 in the open spaces 31 are not centrally arranged. Rather, it is provided that the abutment 25 is arranged offset with respect to an imaginary center line of an open space 31—to the right in FIG. 1. The special abutment 25' is thus closer to the web 15'.

Figure 2:
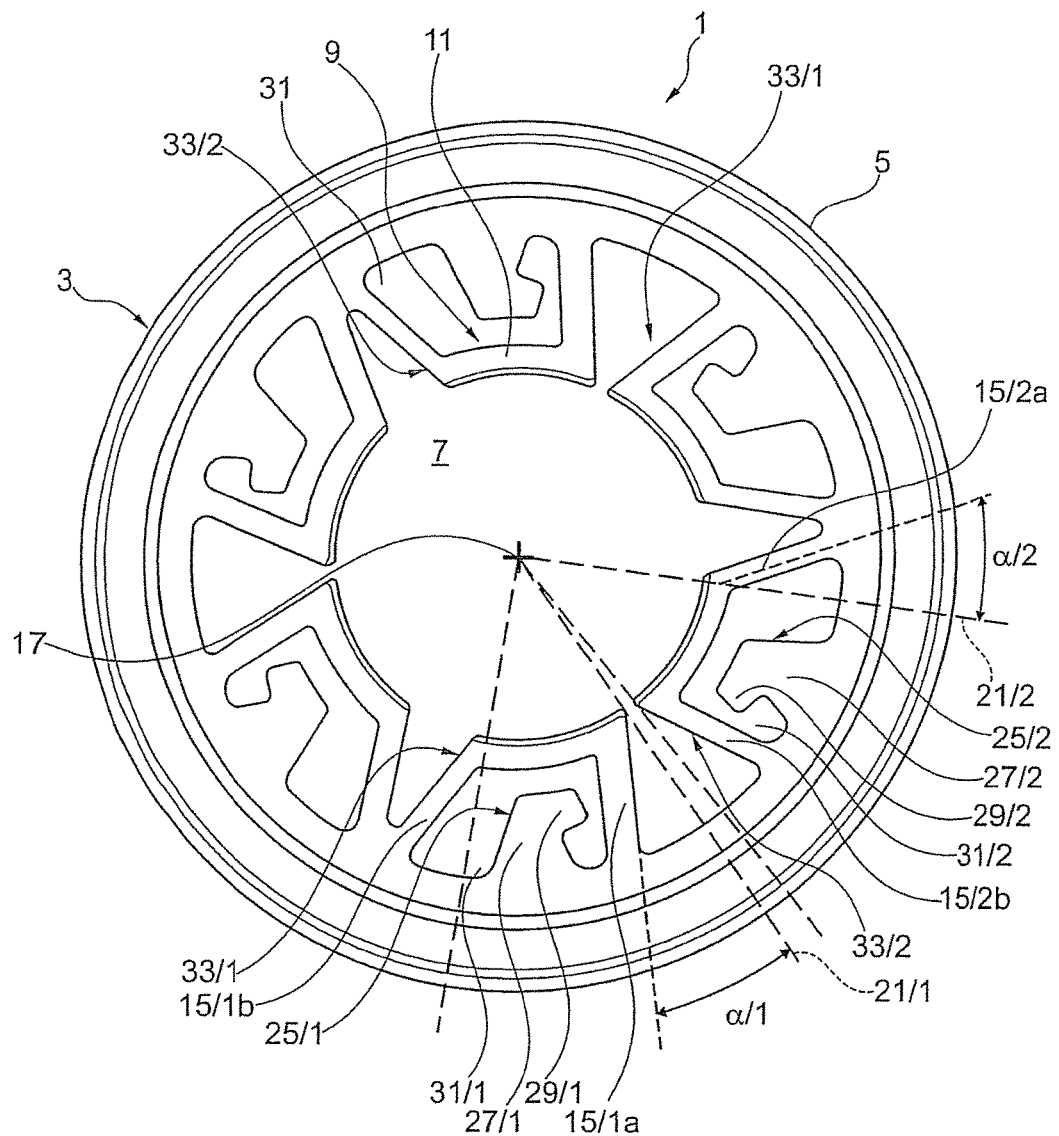
FIG. 2 shows a schematic diagram of a second embodiment of the attachment in a view from below.

FIG. 2 shows a bottom view of a second embodiment of an attachment 1. Identical parts are provided with the same reference characters, and in this regard reference is made to the above description.

It is clear that in the embodiment according to FIG. 2, the inner body 9 is not continuous, i.e. does not comprise the annular inner wall 11, but rather individual ring segments 33 are formed, which each enclose an open space 31. The embodiment of the attachment 1 shown in FIG. 2 comprises two types of ring segments. A first type of ring segment 33/1 comprises a web 15/1a, which encloses with an imaginary radially extending line 21/1 an angle α/1, which opens outward from the central axis 17. Here, the web 15/1 is somewhat left of the line 21/1.

In another type of ring segment 33/2, the associated web 15/2 indicates a direction with respect to an imaginary radially extending line 21/1, and encloses with this line 21/2 an angle α/2 which opens outward from the central axis 17. Here, however, the web 15/2 is somewhat right of the line 21/2.

The open space 31/1 of the first ring segment 31/1 is bounded on the side opposite the web 15/1a by a web 15/1b, which encloses an angle with the web 15/2b, corresponding to web 15' in FIG. 1, so that it extends in turn somewhat left of an imaginary radially extending line. Correspondingly, an open space 31/2 of the ring segment 33/2 is bounded opposite the web 15/2a by a web 15/2b, which encloses an angle with respect to an imaginary radially extending line, so that this web 15/2b is arranged somewhat right of the imaginary line.

In the embodiment shown in FIG. 2, an abutment is provided in each of the open spaces 31/1 and 31/2 enclosed by the ring segments 33/1, 33/2, wherein one abutment 25/1 is allocated to the web 15/1a, and one abutment 25/2 is allocated to the web 15/2b opposite the web 15/2a. Thus, the two abutments 25/1 and 25/2 are again arranged offset with respect to an imaginary center line of the open space.

Both abutments 25/1 and 25/2 are identically formed, as is described with reference to FIG. 1. Thus, they have a base body and a projection extending laterally therefrom, wherein the abutment 25/1 comprises a base body 27/1, from which a projection 29/1 extends, which juts in a counterclockwise direction. The abutment 25/2 is arranged in mirror image: It comprises a base body 27/2, from which a projection 29/2 extends to the left, i.e. in a clockwise direction.

Gaps are respectively provided between the ring segments 31/1 and 31/2, wherein one of the gaps respectively opens in a v-shape into the interior space 7, while the other opens in a v-shape from the inner wall of the ring segment in the direction of the jacket 5. In the latter of the two gaps, i.e. that which opens in a v-shape in the direction of the jacket 5 of the main body 3, an abutment may also be introduced, which comprises a projection, which is either allocated a web 15/1a or 15/2b. In correspondingly large gaps, two abutments may also be provided which are arranged in mirror image to one another. Thus, such abutments would not, as is shown in FIG. 2, support the associated webs outward from the open space 31, but rather outward from the spaces or the gaps between two adjacent ring segments.

In the embodiment shown in FIG. 2, the attachment 1 comprises twelve webs, which are allocated a total of six ring segments.

Figure 3:
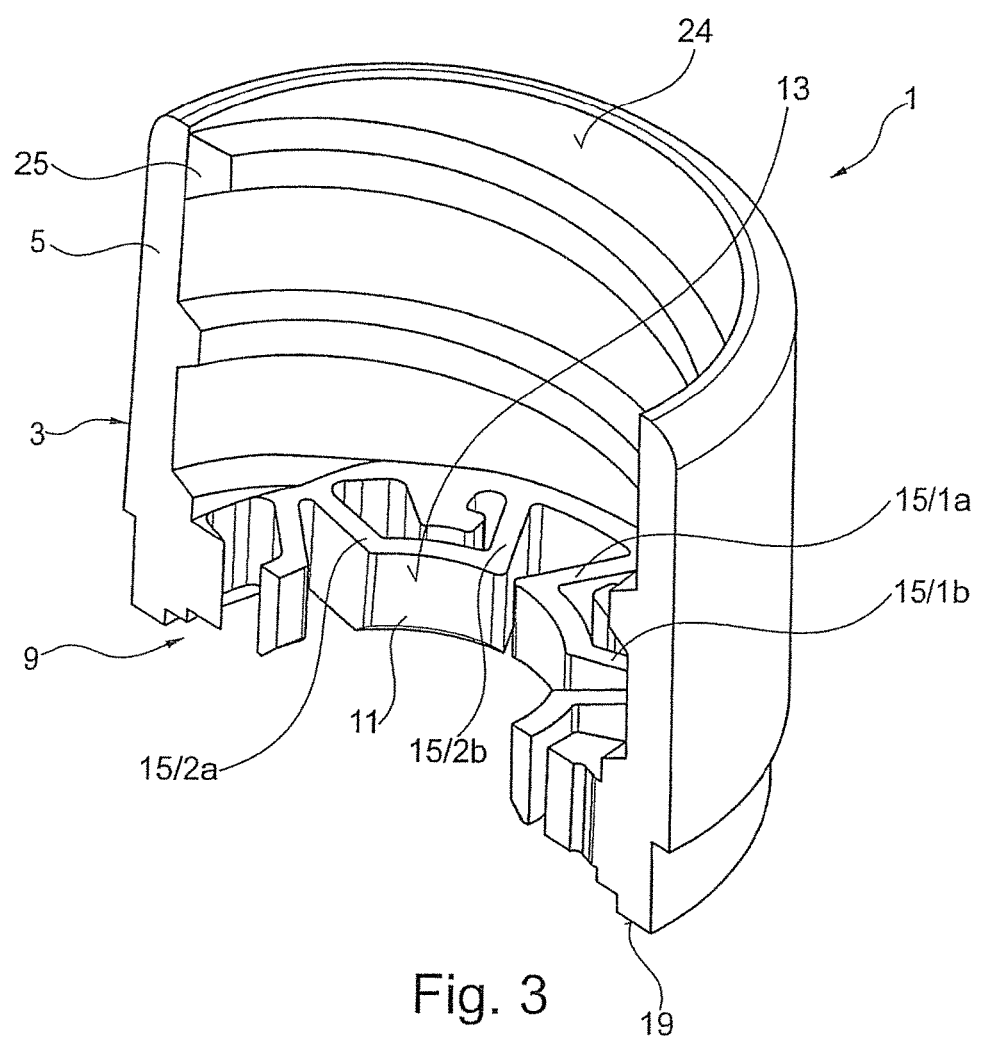
FIG. 3 shows a perspective interior view of the attachment reproduced in FIG. 2.

FIG. 3 shows in perspective view a longitudinal section through the attachment 1 shown in FIG. 2. Identical parts are provided with the same reference characters, and in this regard reference is made to the above description in order to avoid repetitions.

FIG. 3 shows the main body 3 of the attachment with the jacket 5 and with the inner body 9 originating therefrom, which comprises the webs 15/1a, 15/1b, 15/2a and 15/2b originating from the inner side of the jacket 5, between the ends of said webs being located segments of the inner wall 11, which in the attached state of the attachment 1 contact with their interior surfaces 13 the outer surface of a protrusion of a syringe, carpule or the like.

It can be seen in the sectional view according to FIG. 3 that the height of the inner body 9 measured in the vertical direction, i.e. the direction of the central axis 17, not reproduced here, of the attachment 1, is substantially lower than that of the jacket 5, which is provided on its inner side 24 with a thread 35, which has already been mentioned in the above introduction and which will be discussed again in more detail with reference to FIG. 4.

The inner body 9 is arranged at the lower end of the attachment 1, i.e. closer to the underside 19, as this has proven advantageous for the fixing of the attachment 1 on the protrusions of conventional syringes, carpules or the like. If necessary, the inner body 9 can also be displaced upward on the jacket 5 at a distance from the underside 19.

The height of the inner body 9 is selected such that, during attachment of the attachment on a protrusion and in an attempt to rotate this with respect to the protrusion, sufficiently high forces can be built up.

Finally, FIG. 3 shows that the inner body 9 and the jacket 5 lie coaxially in a plane which extends parallel to the underside 19.

Figure 4:
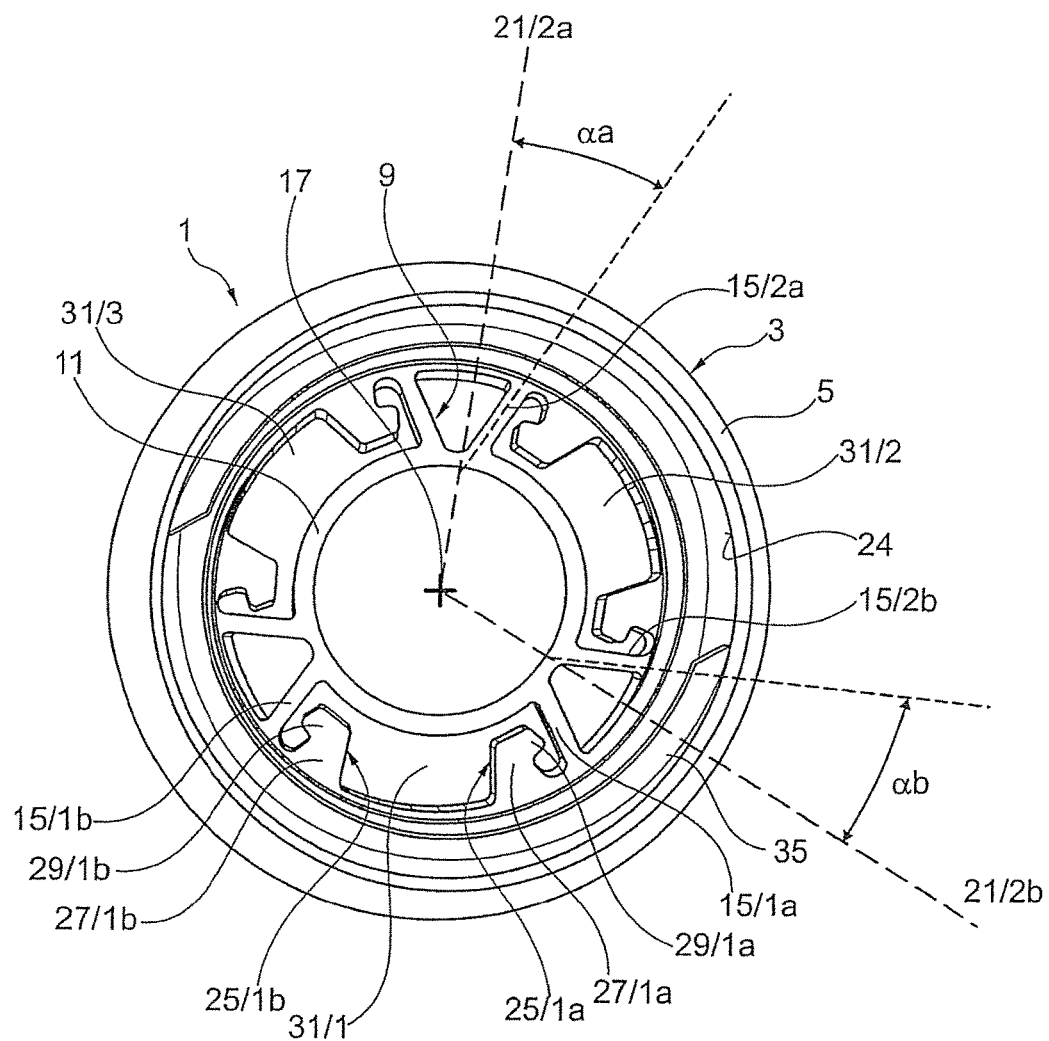
FIG. 4 shows an interior view of a third embodiment of an attachment.

FIG. 4 shows a third exemplary embodiment of an attachment 1 in a top view from above. Again, identical parts are provided with the same reference characters, so that reference is made to the description of the preceding figures.

The attachment 1 comprises a main body 3 having a jacket 5, on the inner side 24 of which a thread 35 is provided, which can interact with an outer thread on the attachment of a cannula or another element. All embodiments of the attachment which have been described herein are preferably provided with such an inner thread. It is, however, also conceivable to provide a bayonet lock or the like for cannulas, attachments of infusion devices or the like.

The attachment 1 comprises an inner body 9, which is provided with an inner wall 11, which is formed continuously here, thus is realized as a ring. The inner wall 11 is connected via webs 15 to the mantle, which is arranged coaxially to the inner body 9, as was also the case in the preceding embodiments.

In the embodiment shown in this figure, six webs are provided, which are allocated to one another in pairs, wherein the pairs are arranged at the same circumferential distance from one another. A first open space 31/1 is bounded by two webs 15/1a and 15/1b, so that the open space 31/1 is enclosed between these, the inner side 24 of the jacket 5 and the inner wall 11.

The attachment 1 as it is shown in FIG. 4 comprises three open spaces 31/1, 31/2 and 31/3, which are all identically formed to the open space 31/1 mentioned directly above. Offset with respect to an imaginary center plane of the open space, which is here designated in short as 31, the abutments 25/1a and 25/1b allocated respectively to the bounding webs 15/1a and 15/1b are arranged, the abutments being formed in mirror image with respect to an imaginary center plane: the abutment 25/1a comprises a projection 29/1a jutting to the right from the base body 27/1, while the abutment 25/1b comprises a projection 29/1b jutting to the left from the base body 27/1b. Both projections point in the direction of the associated web, meaning that projection 29/1a points toward web 15/1a and projection 29/1b toward web 15/1b.

It can be seen from the representation of the open space 31/2 that the first web 15/2a bounding the open space 31/2 encloses with an imaginary radially extending line 21/2a an angle α/a, which opens outward from the central axis 17, wherein the web 15/2a—seen clockwise—advances somewhat ahead of the imagined line 21/2a.

Correspondingly, the second web 15/2b bounding the open space 31/2 encloses with an imaginary radially extending line 21/2b an angle α/b, which opens outward from the central axis 17, wherein the web 15/2b—seen clockwise—lags somewhat behind the line 21/2b.

Between the open spaces are gaps, which are formed as segments of a circle, meaning substantially triangular, wherein the base of this triangle coincides with the inner side 24 of the jacket 5. The point of the triangle opposite the jacket 5 is enclosed by the inner wall 11. In an alternative embodiment of the attachment 1 shown in FIG. 4, the inner wall 11 may here also be discontinuous, so that three identical, separate ring elements are formed.

Below is discussed in greater detail the function of an attachment 1:

Reference is first made to the embodiment according to FIG. 1:

An attachment 1 is attached to a protrusion of a syringe, carpule or the like, such that it finds a secure grip via the inner body 9. The interior surface 13 of the inner wall 11 of the inner body 9 lies firmly against the outer surface of the protrusion, it preferably snaps into a recess provided there, which is in particular formed as a circumferential groove. During attachment on the protrusion, the inner wall 11 is stretched such that frictional forces act between the interior surface 13 and the outer surface of the protrusion.

If now, according to the illustration of FIG. 1, the attachment 1 is rotated counterclockwise as indicated by an arrow P with respect to a protrusion, not shown here, which penetrates the inner wall 11, the inner wall 11 is held due to the frictional forces described above, while the jacket 9 rotates counterclockwise in the direction of the arrow. The web 15' pivots, as do all other webs, counterclockwise about the transition point 23. At the same time, this web 15' pivots in the region of its origin 23', i.e. in the region in which the web 15' originates on the inner side 24 of the jacket 9. Through the pivoting movement of the web 15', this is displaced such that it extends in a radial direction with respect to the central axis 17. The transition point 23 and the origin 23' thus form in a sense bearing points for the web 15', about which this is pivoted though a relative rotation of the jacket 5 with respect to the inner wall 11 of the inner body. Here, the web 15', which comprises a longitudinally stable material, is compressed such that the inner wall 11 is pressed with great force against the outer surface of the protrusion, and thus held fixedly thereagainst.

The same applies for all webs 15 of the attachment 1, which behave as a hinge bar and serve to hold the inner wall 11 of the inner body 9 against a protrusion, secure from rotation by high frictional forces. In order to build up the necessary forces for the compression of the webs, the jacket 5 of the attachment 1 is formed stably.

If the webs are pivoted with respect to the central axis 17 into a radial position, the abutments 25 contact the webs 15, so that further rotational movement of the jacket 5 with respect to the inner wall 11 is prevented.

In order to realize this function, the webs 15 are manufactured from a solid material, so that they can be compressed as much as possible without a substantial reduction in their length. They thereby build up maximal contact forces while they are pivoted from the position shown in FIG. 1 into their radial position.

In order to build up high frictional forces between the interior surface 13 of the inner wall 11 and a protrusion on which the attachment 1 is placed, the interior surface 13 comprises at least regionally a preferably soft material, such as TPE, or consists preferably entirely of this material. It is thus also possible to design the inner wall 11 from a hard material and to line the interior surface 11 with softer materials, or to apply a layer of this soft material.

The webs and regions of the inner wall 11 or the entire interior surface 13 thereof preferably comprise plastic. In particular, it is preferred to manufacture the attachment 1 in a two-component injection molding method from two plastic materials, of which one is hard and resistant to pressure, while the other is soft and thus conforms to the outer surface of the protrusion, which builds up high frictional forces.

In the embodiment according to FIG. 1, all abutments 25 are offset within the open spaces 11 with respect to an imaginary center plane in the direction of one of the webs. The attachment 1 according to FIG. 1 is thus designed such that high resistance against counterclockwise rotation of the jacket 5 with respect to the inner wall 11 is prevented.

It is conceivable in the embodiment of FIG. 1 to arrange at least one, preferably every second abutment 25 in mirror image across an imaginary center plane of the open space 31. In this way, high resistance forces can be built up, and not only during counterclockwise rotation, as has been explained above, but also during clockwise rotation.

In the embodiment shown in FIG. 2, individual ring segments are provided, which are formed alternately in mirror image. The ring segments 33/1 each comprise an abutment 25 which is arranged in an open space 31, namely offset to the right of an imaginary center line. The abutments of the ring segments 33/1 thereby interact respectively with the web 15/1*a*, so that high resistance forces against a counterclockwise rotation of the attachment 1 are built up, as is described with reference to FIG. 1.

As a mirror-image construction is present in the ring segments 31/2, these ring segments 33/2 act against a clockwise rotation of the attachment 1 after attachment on the protrusion of a syringe, carpule or the like.

By means of the mirror-image design of ring segments 33/1 and 33/2, it is thus achieved that this attachment 1 is secured against rotation in both directions.

In consideration of the embodiment of the attachment 1 reproduced in FIG. 4, it is apparent that six webs are provided, of which the webs 15/1*a* and 15/1*b* circumscribe an open space 31/1, wherein this open space is closed in the direction of the central axis 17 by the inner wall 11 and radially outward by the inner surface 24 of the jacket 5.

Near the webs 15/1*a* and 15/1*b* are provided abutments 25/1*a* and 25/1*b* which are formed in mirror image across an imaginary center plane of the open space 31/1 and which are offset to the center plane of the open space 31/1, of which the abutment 25/1*a* comprises a base body 27/1*a*, from which departs a protrusion 29/1 pointing in the direction toward the web 15/1*a*. The projection 29/1*b* correspondingly points toward the web 15/1*b*. During a counterclockwise rotation, the web 15/1*a* is compressed, as is described with reference to FIG. 1, until it is ultimately radially aligned and exerts a maximum compressive force upon the inner wall 11. Further rotation of the attachment 1 is prevented in that the projection 29/1*a* contacts the web 15/1*a* and a further rotation is prevented.

During a rotational movement in the opposite direction, the projection 29/1*b* correspondingly prevents a pivoting of the web 15/1*b* beyond a radial position, because it contacts against the web and prevents further rotation of the attachment 1 with respect to the projection, on which the attachment 1 is placed.

The embodiment shown in FIG. 4 is thus, like that of FIG. 2, secured against clockwise rotation as well as counterclockwise rotation.

The attachment according to the invention is explained here with reference to syringes or carpules. It is clear, however, that it may also be used for other purposes, namely for any desired injection, perfusion, dosing and transfusion devices which can be closed with an attachment of the type discussed herein.

The invention claimed is:

1. An attachment for a syringe or carpule, comprising: a main body enclosing an interior space, into which a protrusion of the syringe or carpule can be inserted, the main body including a jacket surrounding the interior space; and an inner body connected to the jacket and arranged coaxially thereto, the inner body having an inner wall contacting an outer surface of the protrusion of the syringe or carpule in an attached state of the attachment by an interior surface facing the interior space, the inner wall of the inner body connected to the jacket of the attachment by a number of webs, at least one web enclosing an angle together with an imaginary radially extending line, the angle being greater than 0° and acute, the at least one web pivotably connected to the inner wall and to the jacket such that the at least one web extends radially and is compressed between the jacket and the inner wall of the inner body in response to a rotational torque, wherein an open space is enclosed between two adjacent webs, the jacket and the inner wall of the inner body.

2. The attachment according to claim 1, further comprising at least one abutment, which originates from an inner side of the jacket and is arranged at a distance from a web.

3. The attachment according to claim 2, wherein the abutment includes a base body extending out from the inner side of the jacket, the base body including a free end at a distance from the inner side of the jacket.

4. The attachment according to claim 3, wherein the base body tapers from the inner side of the jacket in a direction of its free end.

5. The attachment according to claim 3, wherein the base body includes a lateral projection proximate the free end.

6. The attachment according to claim 1, wherein two abutments are provided.

7. The attachment according to claim 6, wherein the two abutments include at least one projection on each of the outer sides facing away from one another.

8. The attachment according to claim 1, wherein one or two abutments are provided in the open space.

9. The attachment according to claim 8, wherein a gap without an abutment is provided between two circumferentially consecutive open spaces comprising at least one abutment.

10. The attachment according to claim 1, wherein at least two open spaces are provided which are arranged at a distance from one another in a circumferential direction.

11. The attachment according to claim 10, wherein ring segments are formed which each include at least one open space, which is enclosed by two adjacent webs, the jacket and the inner wall of the inner body.

12. The attachment according to claim 11, wherein a ring segment includes two adjacent open spaces.

13. The attachment according to claim 10, wherein at least one abutment is provided in at least one gap between two open spaces.

14. The attachment according to claim 1, wherein a height of the inner body measured in a direction of a central axis of the main body is smaller than a height of the main body.

15. The attachment according to claim 1, wherein the inner wall is discontinuous in a circumferential direction.

16. The attachment according to claim 15, wherein the inner wall includes a plurality of radially spaced apart segments, each segment connected to the jacket by a corresponding pair of the webs.

17. The attachment according to claim 1, wherein the at least one web includes first and second parallel sides extending from the inner body to the jacket.

18. The attachment according to claim 1, wherein each web includes first and second parallel sides extending from the inner body to the jacket.

19. An attachment for a syringe or carpule, the attachment comprising: a main body enclosing an interior space for receiving a portion of the syringe or carpule, the main body including a jacket surrounding the interior space; and an inner body connected to the jacket and arranged coaxially thereto, the inner body having an inner wall radially spaced inward from the jacket and contacting an outer surface of the portion of the syringe or carpule in an attached state of the attachment by an interior surface facing the interior space, the inner wall of the inner body connected to the jacket of the attachment by a plurality of webs, at least one web of the plurality of webs pivotably connected to the inner wall and to the jacket such that the at least one web extends radially and is compressible between the jacket and the inner wall of the inner body in response to a rotational torque, wherein the at least one web includes first and second parallel sides extending from the inner body to the jacket, wherein an open space is enclosed between two adjacent webs, the jacket and the inner wall of the inner body.

\* \* \* \* \*